US011975185B2

(12) United States Patent
Gustavson et al.

(10) Patent No.: US 11,975,185 B2
(45) Date of Patent: *May 7, 2024

(54) WEARABLE CARDIOVERTER DEFIBRILLATOR (WCD) SYSTEM MEASURING PATIENT'S RESPIRATION

(71) Applicant: WEST AFFUM HOLDINGS DAC, Dublin (IE)

(72) Inventors: Laura M. Gustavson, Redmond, WA (US); Kenneth Frederick Cowan, Redmond, WA (US)

(73) Assignee: West Affum Holdings DAC, Dublin (IE)

( * ) Notice: Subject to any disclaimer, the term of this patent is extended or adjusted under 35 U.S.C. 154(b) by 208 days.

This patent is subject to a terminal disclaimer.

(21) Appl. No.: 17/364,357

(22) Filed: Jun. 30, 2021

(65) Prior Publication Data

US 2021/0322759 A1 Oct. 21, 2021

Related U.S. Application Data

(63) Continuation of application No. 15/792,860, filed on Oct. 25, 2017, now Pat. No. 11,052,241.
(Continued)

(51) Int. Cl.
*A61N 1/04* (2006.01)
*A61B 5/00* (2006.01)
(Continued)

(52) U.S. Cl.
CPC .............. *A61N 1/046* (2013.01); *A61B 5/002* (2013.01); *A61B 5/0205* (2013.01);
(Continued)

(58) Field of Classification Search
CPC . A61B 5/0205; A61B 5/02405; A61B 5/0295; A61B 5/04012; A61B 5/0402; A61B 5/053; A61N 1/39; A61N 1/046
See application file for complete search history.

(56) References Cited

U.S. PATENT DOCUMENTS 3,547,106 A 12/1970 Bornmann
3,724,355 A 4/1973 Busch et al.
(Continued)

FOREIGN PATENT DOCUMENTS

DE 19731895 A1 * 4/1998 ......... A61B 5/04011
DE 2005060985 A2 6/2007
(Continued)

OTHER PUBLICATIONS

Heartstart MRx and XL AED Algorithm-Application Note, Jul. 2001, Edition 2 Philips Healthcare, USA.
(Continued)

*Primary Examiner* — Charles A Marmor, II
*Assistant Examiner* — Raymond P Dulman
(74) *Attorney, Agent, or Firm* — Christensen O'Connor Johnson Kindness PLLC

(57) ABSTRACT

A wearable cardioverter defibrillator ("WCD") system may include an impedance detector configured to render an impedance signal of the patient. The WCD system may determine, from the impedance signal, a characteristic of breathing by the patient that can be used as a vital sign. The WCD system may determine, from at least the breathing characteristic, whether or not a shock criterion is met. If the shock criterion is met, the WCD system may control a discharge circuit to discharge a stored electrical charge through the patient. An advantage can be that the breathing characteristic may be used to determine whether or not a patient is experiencing a condition that requires defibrillation therapy, such as sudden cardiac arrest. Even more advantages can be had in discerning the state of the patient when the breathing characteristic is combined with other data, such as from a motion detector.

26 Claims, 8 Drawing Sheets

Related U.S. Application Data

(60) Provisional application No. 62/417,147, filed on Nov. 3, 2016.

(51) Int. Cl.
  *A61B 5/0205* (2006.01)
  *A61N 1/39* (2006.01)
  *A61B 5/024* (2006.01)
  *A61B 5/0295* (2006.01)
  *A61B 5/316* (2021.01)
  *A61B 5/318* (2021.01)

(52) U.S. Cl.
  CPC ......... *A61N 1/3904* (2017.08); *A61N 1/3925* (2013.01); *A61B 5/02405* (2013.01); *A61B 5/0295* (2013.01); *A61B 5/316* (2021.01); *A61B 5/318* (2021.01); *A61N 1/0484* (2013.01); *A61N 1/3968* (2013.01)

(56) References Cited

U.S. PATENT DOCUMENTS

| | | |
|---|---|---|
| 4,583,524 A | 4/1986 | Hutchins |
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,628,757 B1 | 12/2009 | Koh |
| 7,753,759 B2 | 7/2010 | Pintor et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,417,327 B2 | 4/2013 | Chapman et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 2002/0181680 A1 | 12/2002 | Linder et al. |
| 2003/0158593 A1 | 8/2003 | Heilman et al. |
| 2005/0085865 A1 | 4/2005 | Tehrani |
| 2005/0107833 A1 | 5/2005 | Freeman et al. |
| 2005/0107834 A1 | 5/2005 | Freeman et al. |
| 2005/0115561 A1 | 6/2005 | Stahmann et al. |
| 2006/0036183 A1 | 2/2006 | Sackner et al. |
| 2006/0173499 A1 | 8/2006 | Hampton et al. |
| 2008/0275349 A1* | 11/2008 | Halperin ................ A61B 5/447 600/364 |
| 2008/0312709 A1 | 12/2008 | Vollpe et al. |
| 2009/0005827 A1 | 1/2009 | Weintraub et al. |
| 2009/0024176 A1 | 1/2009 | Yun et al. |
| 2009/0204166 A1 | 8/2009 | Bharmi |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0112419 A1 | 5/2011 | Bjorling et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0043149 A1 | 2/2014 | Cowan et al. |

(56) References Cited

U.S. PATENT DOCUMENTS

| | | | |
|---|---|---|---|
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0257426 A1 | 9/2014 | Arcot-Krishnamurthy et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0059023 A1 | 3/2016 | Freeman et al. |
| 2016/0074667 A1 | 3/2016 | Sullivan et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0256104 A1 | 9/2016 | Romem et al. |
| 2016/0283900 A1 | 9/2016 | Johnson et al. |
| 2016/0287122 A1 | 10/2016 | Heneghan |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0095673 A1 | 4/2017 | Ludwig et al. |
| 2017/0162840 A1 | 6/2017 | Pendry |
| 2017/0319862 A1 | 11/2017 | Foshee, Jr. et al. |
| 2017/0367591 A1 | 12/2017 | Jorgensen |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |
| 2018/0361165 A1 | 12/2018 | Jaax et al. |
| 2019/0030352 A1 | 1/2019 | Sullivan et al. |
| 2019/0076666 A1 | 3/2019 | Medema |
| 2019/0116896 A1 | 4/2019 | Armour et al. |
| 2019/0321650 A1 | 10/2019 | Raymond et al. |

FOREIGN PATENT DOCUMENTS

| | | |
|---|---|---|
| EP | 2305110 A1 | 4/2011 |
| JP | 4320257 A | 3/2005 |
| JP | 5963767 A | 1/2014 |
| JP | 2014526282 A | 10/2014 |
| WO | 98/39061 A2 | 9/1998 |
| WO | 2011/146448 A1 | 11/2011 |
| WO | 2012/064604 A1 | 5/2012 |
| WO | 2012/151160 A1 | 11/2012 |
| WO | 2015/056262 A1 | 4/2015 |

OTHER PUBLICATIONS

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

H. Kenneth Walker, Md, W Dalls Hall, Md and J Willis Hurst, Md, Clinical Methods: The History, Physical, and Laboratory Examinations, $3^{rd}$ edition, The History, Physical, and Laboratory Examinations, Chapter 11 portion, Dyspnea, Orthopnea, and Paroxysmal Noctural Dyspnea, 1990, Butterworth Publishers, a division of Reed Publishing.

Gupta, Amit K., Respiration Rate Measurement Based on Impedance Pneumography, Application Report SBAA181, Feb. 2011, pp. 1-11, Texas Instruments Incorporated, Dallas, Texas.

Boehmer, M.D., John P., New Sensors in CIED Devices, Presentation, Jan. 2015, pp. 1-19, Penn State College of Medicine.

Boehmer, M.D., John P., Nonhemodynamic Parameters from Implantable Devices for Heart Failure Risk Stratification, Heart Failure Clin. 11 (2015), pp. 191-201, Elsevier Inc.

Forleo, Giovanni B. et al., Long-term monitoring of respiratory rate in patients with heart failure: the Multiparametric Heart Failure Evaluation in Implantable Cardioverter-Defibrillator Patients (Multitude-HF) study, J. Interv. Card. Electrophysiol., Aug. 2015, 43(2):135-144.

Goetze, S. et al., Ambulatory respiratory rate trends identify patients at higher risk of worsening heart failure in implantable cardioverter defibrillator and biventricular device recipients: a novel ambulatory parameter to optimize heart failure management, J. Interv. Card. Electrophysiol. (2015) 43, pp. 21-29, Springer.

\* cited by examiner

*SAMPLE COMPONENTS OF WEARABLE CARDIOVERTER DEFIBRILLATOR (WCD) SYSTEM*

SAMPLE COMPONENTS OF EXTERNAL DEFIBRILLATOR

*METHODS*

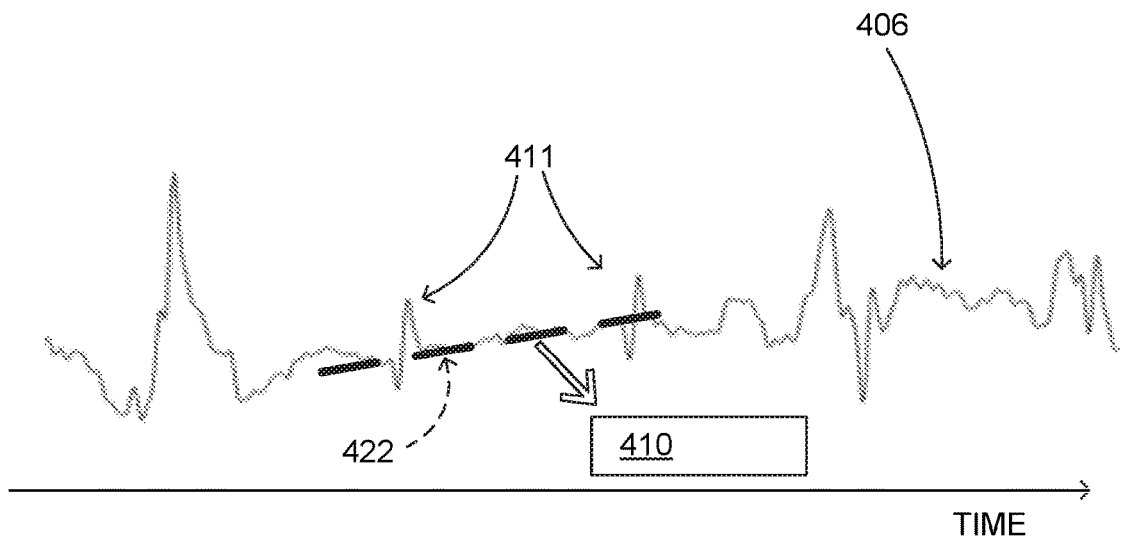
FIG. 4A  *IDENTIFIED SHIFTING BASELINE OF SAMPLE RENDERED ECG SIGNAL USED IN FILTERING OPERATION*
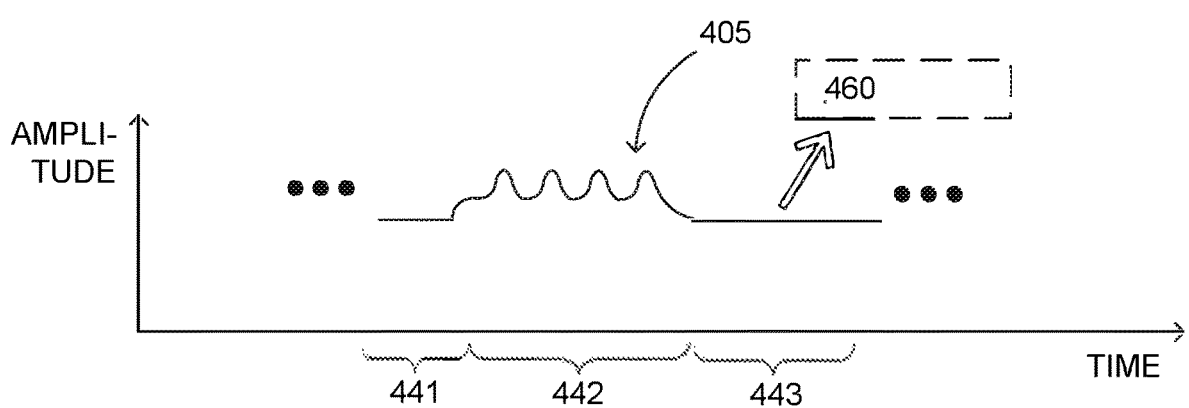
FIG. 4B  *SAMPLE MOTION DETECTION SIGNAL OR INPUT*

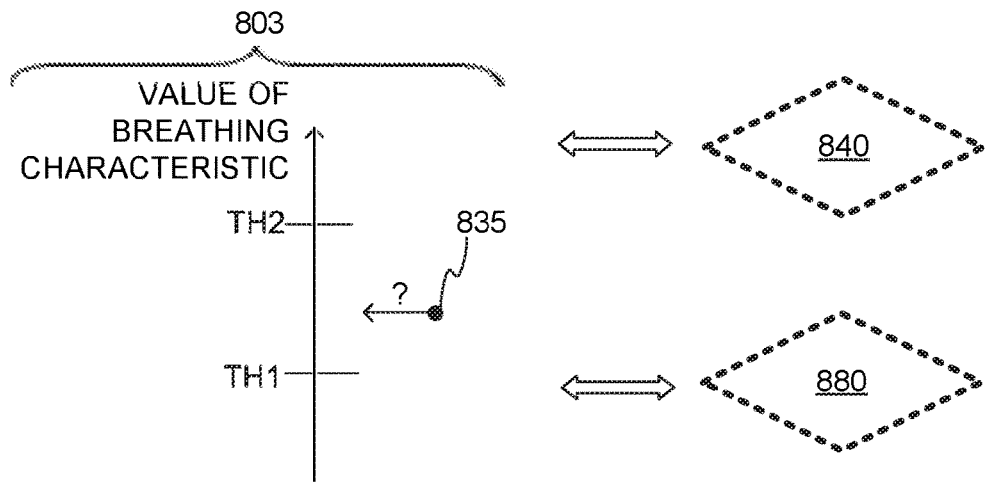
FIG. 8  *BREATHING CHARACTERISTIC VALUE RELATIVE TO THRESHOLDS AND RANGES*
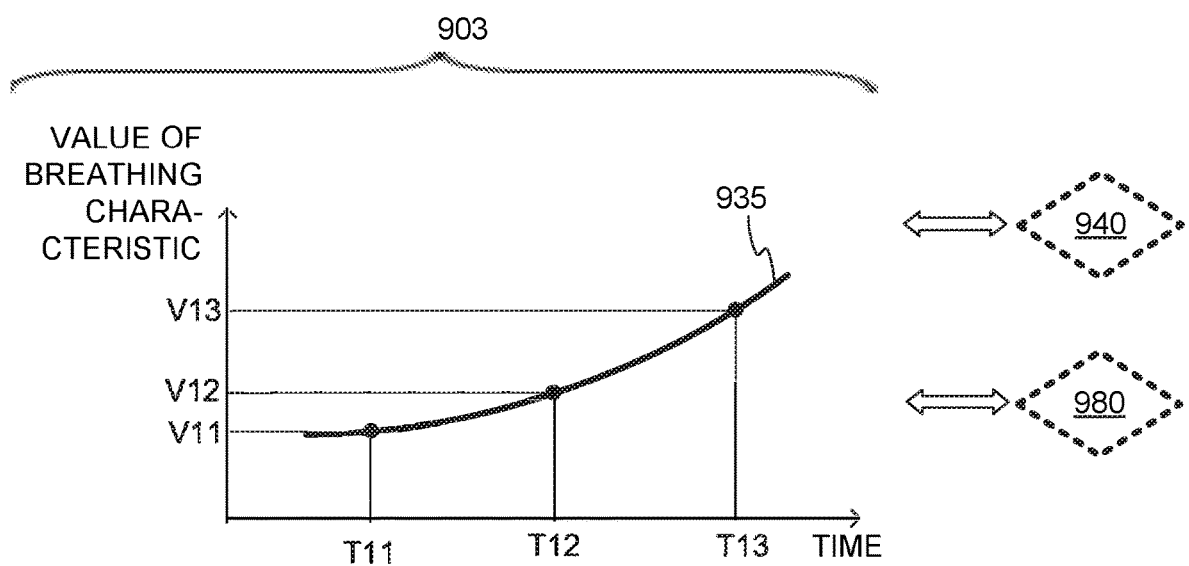
FIG. 9  *BREATHING CHARACTERISTIC CHANGING VALUE OVER TIME*

WEARABLE CARDIOVERTER DEFIBRILLATOR (WCD) SYSTEM MEASURING PATIENT'S RESPIRATION

CROSS REFERENCE TO RELATED PATENT APPLICATIONS

This patent application is a Continuation Application of co-pending U.S. patent application Ser. No. 15/792,860, filed Oct. 25, 2017, which claims priority from U.S. Provisional Patent Application Ser. No. 62/417,147, filed on Nov. 3, 2016, the disclosure of each application which, as initially made, is hereby incorporated by reference.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g. within 10 minutes, unless treated in the interim.

Some people have an increased risk of SCA. People at a higher risk include patients who have had a heart attack, or a prior SCA episode. A frequent recommendation is for these people to receive an Implantable Cardioverter Defibrillator (ICD). The ICD is surgically implanted in the chest, and continuously monitors the patient's electrocardiogram (ECG) signal, which is sometimes simply called ECG. If certain types of heart arrhythmias are detected, then the ICD delivers an electric shock through the heart.

After being identified as having an increased risk of an SCA, and before receiving an ICD, these people are sometimes given a Wearable Cardioverter Defibrillator (WCD) system. (Early versions of such systems were called wearable cardiac defibrillator systems.) A WCD system typically includes a harness, vest, or other garment that the patient is to wear. The WCD system further includes electronic components, such as a defibrillator and electrodes, coupled to the harness, vest, or other garment. When the patient wears the WCD system, the external electrodes may then make good electrical contact with the patient's skin, and therefore can help determine the patient's ECG. If a shockable heart arrhythmia is detected, then the defibrillator delivers the appropriate electric shock through the patient's body, and thus through the heart.

One of the challenges in developing a WCD system is to determine accurately what patient is experiencing, and therefore to determine whether or not they require defibrillation therapy. With ambulatory patients, there are many sources of noise that can make this difficult by analyzing the ECG waveform alone.

All subject matter discussed in this Background section of this document is not necessarily prior art, and may not be presumed to be prior art, simply because it is presented in this Background section. Plus, any reference to any prior art in this description is not, and should not be taken as, an acknowledgement or any form of suggestion that such prior art forms parts of the common general knowledge in any country or any art. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventors. This approach in and of itself may also be inventive.

BRIEF SUMMARY

The present description gives instances of Wearable Cardioverter Defibrillator (WCD) systems, storage media that store programs, and methods, the use of which may help overcome problems and limitations of the prior art.

In embodiments, a wearable cardioverter defibrillator ("WCD") system includes an impedance detector configured to render an impedance signal of the patient. The WCD system may determine, from the impedance signal, a characteristic of breathing by the patient that can be used as a vital sign. The WCD system may determine, from at least the breathing characteristic, whether or not a shock criterion is met. If the shock criterion is met, the WCD system may control a discharge circuit to discharge a stored electrical charge through the patient.

An advantage can be that the breathing characteristic may be used to determine whether or not a patient is experiencing a condition that requires defibrillation therapy, such as sudden cardiac arrest. Even more advantages can be had in discerning the state of the patient when the breathing characteristic is combined with other data, such as from a motion detector.

These and other features and advantages of the claimed invention will become more readily apparent in view of the embodiments described and illustrated in the present disclosure, namely from the present written specification and the drawings.

BRIEF DESCRIPTION OF THE DRAWINGS

FIG. 4A is a time diagram of a sample rendered ECG signal, further annotated to indicate a shifting baseline that may be identified and used in filtering operations according to embodiments.

FIG. 4B is a time diagram of a sample rendered motion detection signal or input, further annotated to indicate an identified motionless time period, during which a baseline value of a breathing characteristic may be determined according to embodiments.

FIG. 8 illustrates how a sample value of a determined breathing characteristic may be used for performing operations according to embodiments.

FIG. 9 illustrates how changes in a sample value of a determined breathing characteristic may be used for performing operations according to embodiments.

DETAILED DESCRIPTION

As has been mentioned, the present description is about Wearable Cardioverter Defibrillator (WCD) systems, storage media that store programs, and methods. Embodiments are now described in more detail.

A wearable cardioverter defibrillator (WCD) system made according to embodiments has a number of components. These components can be provided separately as modules that can be interconnected, or can be combined with other components, etc.

Figure 1:
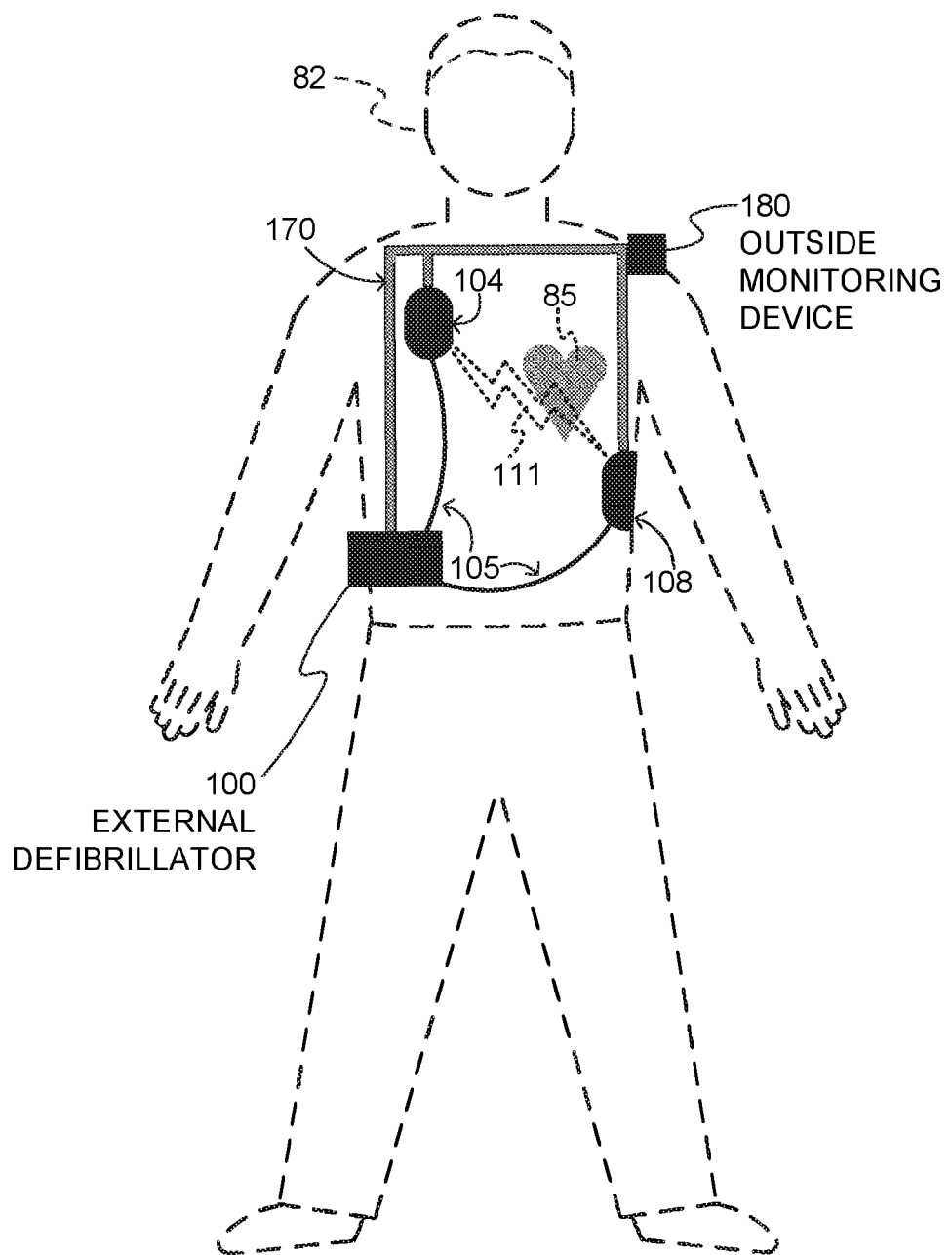
FIG. 1 is a diagram of components of a sample wearable cardioverter defibrillator (WCD) system, made according to embodiments.

FIG. 1 depicts a patient 82. Patient 82 may also be referred to as a person and/or wearer, since that patient wears components of the WCD system. Patient 82 is ambulatory, which means patient 82 can walk around, and is not necessarily bed-ridden.

FIG. 1 also depicts components of a WCD system made according to embodiments. One such component is a support structure 170 that is wearable by patient 82. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to parallel articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient by adhesive material, for example as shown in U.S. Pat. No. 8,024,037. Support structure 170 can even be implemented as described for the support structure of US Pat. App. No. US 2017/0056682 A1, which is incorporated herein by reference. Of course, in such embodiments, the person skilled in the art will recognize that additional components of the WCD system can be in the housing of a support structure instead of being attached externally to the support structure, for example as described in the 2017/0056682 document. There can be other examples.

A WCD system according to embodiments is configured to defibrillate a patient who is wearing it, by delivering an electrical charge to the patient's body in the form of an electric shock delivered in one or more pulses. FIG. 1 shows a sample external defibrillator 100, and sample defibrillation electrodes 104, 108, which are coupled to external defibrillator 100 via electrode leads 105. Defibrillator 100 and defibrillation electrodes 104, 108 can be coupled to support structure 170. As such, many of the components of defibrillator 100 could be therefore coupled to support structure 170. When defibrillation electrodes 104, 108 make good electrical contact with the body of patient 82, defibrillator 100 can administer, via electrodes 104, 108, a brief, strong electric pulse 111 through the body. Pulse 111, also known as shock, defibrillation shock, therapy or therapy shock, is intended to go through and restart heart 85, in an effort to save the life of patient 82. Pulse 111 can further include one or more pacing pulses, and so on.

A prior art defibrillator typically decides whether to defibrillate or not based on an ECG signal of the patient. However, external defibrillator 100 may initiate defibrillation (or hold-off defibrillation) based on a variety of inputs, with ECG merely being one of them.

Accordingly, it will be appreciated that signals such as physiological signals containing physiological data can be obtained from patient 82. While the patient may be considered also a "user" of the WCD system, this is not a requirement. That is, for example, a user of the wearable cardioverter defibrillator (WCD) may include a clinician such as a doctor, nurse, emergency medical technician (EMT) or other similarly situated individual (or group of individuals). The particular context of these and other related terms within this description should be interpreted accordingly.

The WCD system may optionally include an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document. Device 180 may include one or more transducers or sensors that are configured to render one or more physiological inputs or signals from one or more patient parameters that they sense.

Optionally, device 180 is physically coupled to support structure 170. In addition, device 180 can be communicatively coupled with other components, which are coupled to support structure 170. Such communication can be implemented by a communication module, as will be deemed applicable by a person skilled in the art in view of this description.

Figure 2:
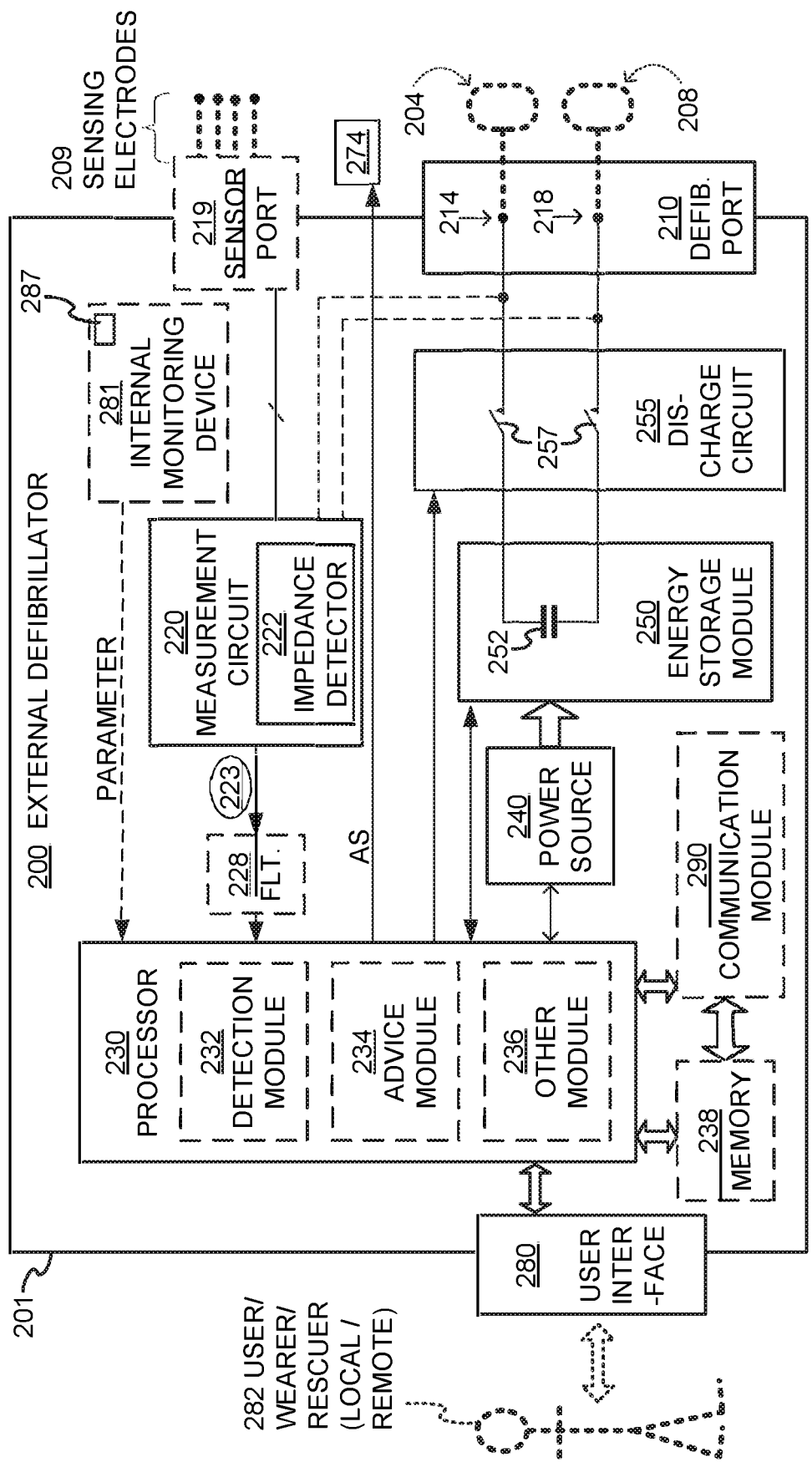
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications. There are many examples of output devices. For example, an output device can be a light, or a screen to display what is sensed, detected and/or measured, and provide visual feedback to rescuer 282 for their resuscitation attempts, and so on.

Another output device can be a speaker, which can be configured to issue voice prompts, beeps, loud alarm sounds and/or words to warn bystanders, etc.

User interface 280 may further include input devices for receiving inputs from users. Such input devices may additionally include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more transducers or sensors that are configured to render one or more physiological inputs from one or more patient parameters that it senses.

Patient parameters may include patient physiological parameters. Patient physiological parameters may include, for example and without limitation, those physiological parameters that can be of any help in detecting by the wearable defibrillation system whether the patient is in need of a shock, plus optionally their medical history and/or event history. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an $SpO_2$ sensor, and so on. In view of this disclosure, it will be appreciated that such sensors can help detect the patient's pulse, and can therefore also be called pulse detection sensors, pulse sensors, and pulse rate sensors. Pulse detection is also taught at least in Physio-Control's U.S. Pat. No. 8,135,462, which is hereby incorporated by reference in its entirety. In addition, a person skilled in the art may implement other ways of performing pulse detection. In such cases, the transducer includes an appropriate sensor, and the physiological input is a measurement by the sensor of that patient parameter. For example, the appropriate sensor for a heart sound may include a microphone, etc.

In some embodiments, the local parameter is a trend that can be detected in a monitored physiological parameter of patient 282. A trend can be detected by comparing values of parameters at different times. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$ or $CO_2$; f) respiratory function, respiration rate, etc.; g) motion, level of activity; and so on. Once a trend is detected, it can be stored and/or reported via a communication link, along perhaps with a warning. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281.

A motion detector of a WCD system according to embodiments can be configured to detect a motion event, or motion in general. In response, the motion detector may render or generate, from the detected motion event or motion, a motion detection input or signal that can be received by a subsequent device or functionality. A motion event can be defined as is convenient, for example a change in motion from a baseline motion or rest, etc. In such cases, the patient parameter is a motion.

System parameters of a WCD system can include system identification, battery status, system date and time, reports of self-testing, records of data entered, records of episodes and intervention, and so on.

Environmental parameters can include ambient temperature and pressure. Moreover, a humidity sensor may provide information as to whether it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, such as a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal or an impedance signal. The ECG signal may be, for example, a 12-lead signal, or a signal from a different number of leads, especially if they make good electrical contact with the body of the patient. Sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrode and the skin. Electrically speaking, when the fluid is deployed, the electrical impedance between the electrode and the skin is reduced. Mechanically speaking, the fluid may be in the form of a low-viscosity gel, so that it does not flow away from the electrode, after it has been deployed. The fluid can be used for both defibrillation electrodes 204, 208, and for sensing electrodes 209.

The fluid may be initially stored in a fluid reservoir, not shown in FIG. 2, which can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations, to which the electrodes are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the physiological input may reflect an ECG measurement. The patient parameter can be an ECG, which can be sensed as a voltage difference between electrodes 204, 208.

Measurement circuit 220 may also include an impedance detector 222. As such, the patient parameter can be an impedance, which can be sensed between electrodes 204, 208 and/or the connections of sensor port 219. Sensing the impedance can be useful for detecting, among other things, whether these electrodes 204, 208 and/or sensing electrodes 209 are not making good electrical contact with the patient's body. In embodiments, impedance detector 222 is configured to render an impedance signal 223 of the patient. The impedance signal can be rendered as a modulation to a carrier signal, as a stream of values, and so on.

These patient physiological signals can be sensed, when available. Measurement circuit 220 can then render or generate information about them as physiological inputs, data, other signals, etc. More strictly speaking, the information rendered by measurement circuit 220 is output from it, but this information can be called an input because it is received by a subsequent device or functionality as an input.

In some embodiments, defibrillator 200 also includes a stand-alone filter 228. Filter 228 can be configured to receive signals rendered by measurement circuit 220, such as the ECG signal, impedance signal 223, and so on. Filter 228 can be configured to derive a filtered impedance signal from the rendered impedance signal. The filtered impedance signal may correspond to the rendered impedance signal, with at least a portion of the rendered impedance signal changed. Alternately, filtering signals may be accomplished by processing numbers within a processor, such as is described below.

Defibrillator 200 also includes a processor 230. Processor 230 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as physiological inputs, data, or other signals, may be used by the VF detector to determine whether the patient is experiencing VF. Detecting VF is useful, because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments, and determining whether a shock criterion is met. The determination can be made from a rhythm analysis of the captured ECG signal or otherwise.

In some embodiments, when the determination is to shock, an electrical charge is delivered to the patient. Delivering the electrical charge is also known as discharging. Shocking can be for defibrillation, pacing, and so on.

Processor 230 can include additional modules, such as other module 236, for other functions. In addition, if internal monitoring device 281 is indeed provided, it may be operated in part by processor 230, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. In some embodiments, power source 240 is controlled by processor 230. Appropriate components may be included to provide for charging or replacing power source 240.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

Defibrillator 200 moreover includes a discharge circuit 255. When the decision is to shock, processor 230 can be configured to control discharge circuit 255 to discharge through the patient the electrical charge stored in energy storage module 250. When so controlled, circuit 255 can permit the energy stored in module 250 to be discharged to nodes 214, 218, and from there also to defibrillation electrodes 204, 208, so as to cause a shock to be delivered to the patient. Circuit 255 can include one or more switches 257. Switches 257 can be made in a number of ways, such as by an H-bridge, and so on. Circuit 255 can also be controlled via user interface 280.

Defibrillator 200 can optionally include a communication module 290, for establishing one or more wired or wireless communication links with other devices of other entities, such as a remote assistance center, Emergency Medical Services (EMS), and so on. The data can include patient data, event information, therapy attempted, CPR performance, system data, environmental data, and so on. For example, communication module 290 may transmit wirelessly, on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. In addition, communication module 290 may also have the capability to contact emergency services when an episode of sudden cardiac death is detected or other critical illnesses are detected. Module 290 may also include such interconnected sub-components as may be deemed necessary by a person skilled in the art, for example an antenna, portions of a processor, supporting electronics, outlet for a telephone or a network cable, etc. This way, data, commands, etc. can be communicated.

Defibrillator 200 can optionally include other components.

Returning to FIG. 1, in embodiments, one or more of the components of the shown WCD system have been customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. Such baseline physiological parameters can be used to customize the WCD system, in order to make its diagnoses more accurate, since the patients' bodies differ from one another. Of course, such parameters can be stored in a memory of the WCD system, and so on.

A programming interface can be made according to embodiments, which receives such measured baseline physiological parameters. Such a programming interface may input automatically in the WCD system the baseline physiological parameters, along with other data.

The devices and/or systems mentioned in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs.

Methods are now described.

Figure 3:
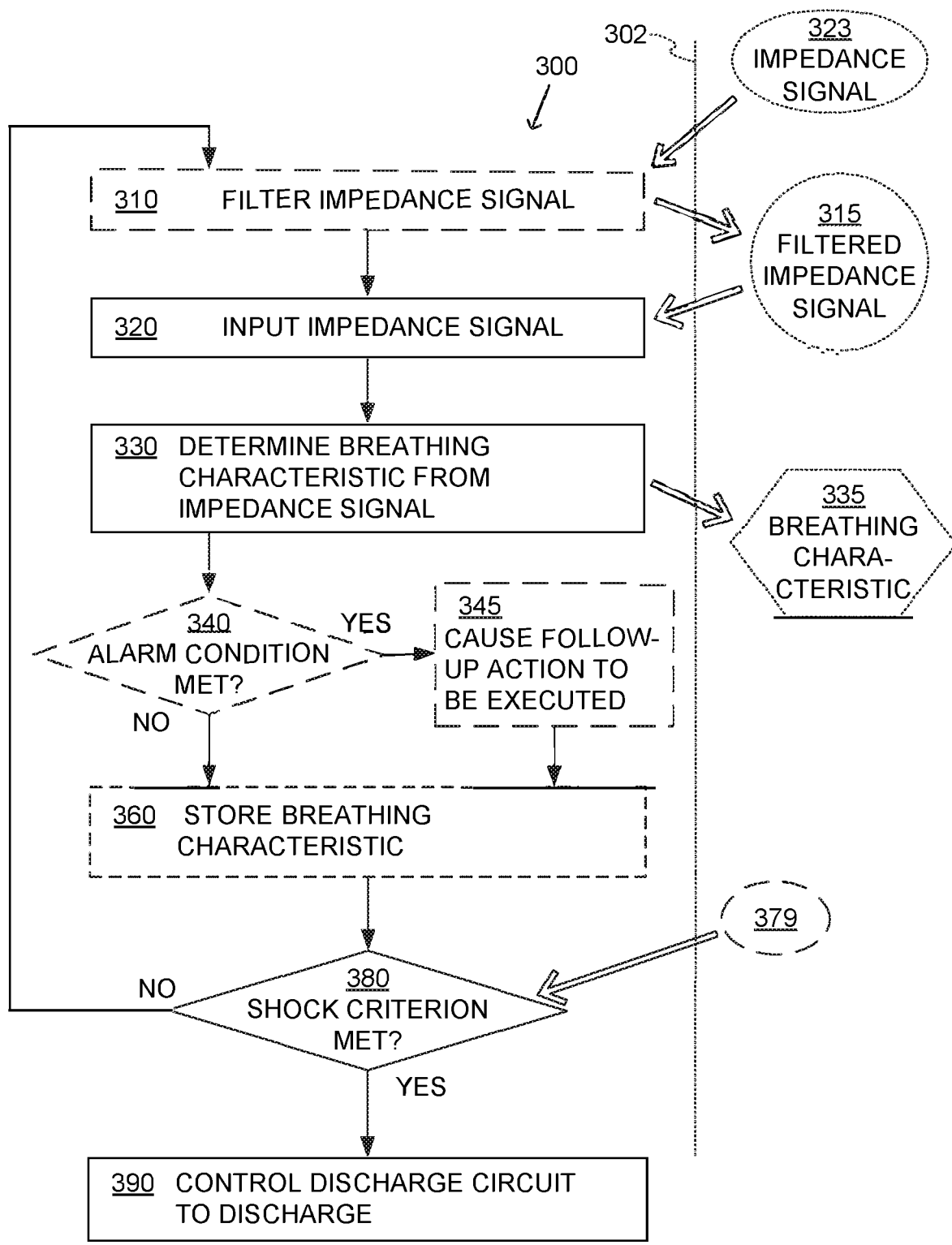
FIG. 3 shows a flowchart for illustrating methods according to embodiments, the flowchart annotated with icons of elements that can be related to individual operations of the flowchart.

FIG. 3 shows a flowchart 300 for illustrating methods according to embodiments. Flowchart 300 includes operations that are linked by arrows. A vertical line 302 is at the right side of flowchart 300. Further to the right of vertical line 302 are shown icons of elements that can be related to individual operations of flowchart 300. These icons are indicated as linked with their respective operations by using wider arrows that cross line 302. These wider arrows, however, do not form part of flowchart 300.

FIG. 3 starts with an optional operation 310, according to which a rendered impedance signal 323 may be filtered, to derive a filtered impedance signal 315. Rendered impedance signal 323 may be the impedance signal rendered by an impedance detector, such as impedance signal 223.

The filtering of operation 310 may be performed in a number of ways. For example, filtered impedance signal 315 may be derived by removing from rendered impedance signal 323 variations that have a frequency greater than a threshold frequency, such as 10 Hz. Or, filtered impedance signal 315 may be derived by removing from rendered impedance 323 signal variations that repeat over a period of at least 30 seconds.

In some embodiments, filtering is informed by another, concurrent signal from another transducer. Two examples are developed in this document, although more are possible.

First, referring tentatively to FIG. 4A, a WCD system may further include a transducer configured to render an electrocardiogram (ECG) signal 406 of the patient, such as sensing electrodes 209 in combination with measurement circuit 220, etc. In signal 406, QRS complexes 411 maybe identified. In addition, variations in a baseline of ECG signal 406 may be identified. For example, a line segment 422 shows an instance where the baseline of signal 406 is shifting. In this instance, line segment 422 is largely defined between the two identified QRS complexes 411, but that is coincidental; in fact, such line segments may be defined at other times of signal 406. The filtered impedance signal, then, may be derived by removing from the rendered impedance signal variations that are concurrent with the identified variations of ECG signal 406, variations such as indicated by line segment 422. In other words, the slope of line segment 422 may inform a filtering operation 410, which may be performed as operation 310.

For a second example, a WCD system may further include a motion detector, such as was described above. Variations may be identified in the motion detection signal. The filtered impedance signal may be derived by removing from the rendered impedance signal variations that are concurrent with the identified variations in the motion detection signal.

Returning to FIG. 3, after optional operation 310, according to another operation 320, an impedance signal of the patient may be input. The impedance signal input at operation 320 may be rendered impedance signal 323, if optional operation 310 is not performed. Alternately, the impedance signal input at operation 320 may be filtered impedance signal 315, instead of rendered impedance signal 323.

According to another operation 330, a characteristic of breathing 335 by the patient may be determined from the impedance signal input at operation 320. If operation 310 has been performed, characteristic 335 is determined from filtered impedance signal 315, instead of from rendered impedance signal 323.

According to another, optional operation 340, it may be determined whether or not breathing characteristic 335 meets an alarm condition. If the answer at operation 340 is YES then, according to another, optional operation 345, a follow-up action may be caused to be executed. In other words, the follow-up action may be caused to be executed responsive to determining that the alarm condition is thus met at operation 340. Examples are given later in this document.

After operation 345, or if the answer at operation 340 is NO then, according to another, optional operation 360, a value of breathing characteristic 335 may be stored in a memory, such as memory 238. Note that this operation 360 may store values as a matter of record. In some instances, some of these stored values may be used to form a baseline for comparison.

According to another operation 380, it may be determined whether or not a shock criterion is met. If at operation 380 the answer is NO, then execution may return to a previous operation, such as operation 310. Else, if at operation 380 the answer is YES, then according to another operation 390, a discharge circuit such as discharge circuit 255 may be controlled to discharge stored electrical charge through the patient, while the support structure is worn by the patient. This would deliver electrical therapy.

The determination of operation 380 may be further performed in a number of ways. Examples are now described.

In some embodiments, the determination of operation 380 is performed from at least breathing characteristic 335. For instance, a baseline value for breathing characteristic 335 may be stored in a memory, such as memory 238. Then a difference may be computed of a current value of the breathing characteristic and the stored baseline value. Then it may be determined at least in part that the shock criterion is met, responsive to the computed difference being larger than a threshold.

A baseline value for breathing characteristic 335 may be a set value, or a value customized to the patient by training the WCD system or by separately evaluating the patient. For example, referring now to FIG. 4B, a time diagram is shown of a sample rendered motion detection signal 405, which is also called motion detection input 405. Three time domains 441, 442, 443 are identified. A motion event is detected in time domain 442. Signal 405 could indicate that the patient rose from a chair, walked four steps to another chair, and then sat down again. Motionlessness is detected in time domains 441 & 443. In such embodiments, a baseline value for breathing characteristic 335 may be determined from a portion of an impedance signal, to be discussed later, in view of a portion of motion detection signal 405 relative to the portion of the impedance signal. For example, time domain 443 of motionlessness may be used to inform when a storing operation 460 may be performed for purposes of developing a baseline. Otherwise, operation 460 may be performed as described for operation 360. As such, the above-mentioned portion of the impedance signal may be concurrent with a portion of motion detection signal 405 that is motionless, such as during time periods 441 & 443, or presumed walking, such as during time period 442, and so on. Different baseline values may be stored for different activities.

In some embodiments, the determination of operation 380 is performed from also another input 379. Input 379 may be derived from a transducer configured to render an input from a sensed parameter of the patient, the input being distinct from the impedance signal. The processor may be able to determine from at least input 379 and breathing characteristic 335 whether or not the shock criterion is met. Two particular examples are now described, although more are possible.

As a first example, input 379 can be an input of the motion detector mentioned above. The processor can be configured to determine from at least the motion detection signal and breathing characteristic 335 whether or not the shock criterion is met. For instance, a motion detection input 379 that includes a sudden motion of large amplitude during the day or while walking, followed by lack of any motion thereafter, may indicate SCA, where the patient dropped and has remained motionless. In such an instance, motion detection input 379 may also be used for performing operation 380.

The combination of motion detection signal 405 may resolve ambiguities, especially given that the ECG signal is often hampered by electrical noise. For example, motion detection signal 405 may be used to qualify an abnormally high detected heart rate, to determine if it is being caused by strenuous physical exercise or an emerging illness. Variations of the raw impedance signal can be analyzed to look for correlated variation on the ECG signal to indicate noise caused by electrode movement. Moreover, the raw, rendered impedance signal used to determine the respiration rate can be used by the processor's algorithm to help determine if a fast rate detected on the ECG signal is an actual cardiac signal, or noise that is being caused by movement of the electrodes. Movement of the electrodes may also cause variations in impedance, and if the impedance variation can be correlated to the fast rate seen on the ECG then that is an indicator the fast rate is actually noise caused by motion and not a VT or VF rhythm. An abnormal respiration rate can be used by the defibrillation therapy algorithm to trigger more processor intensive analysis of the ECG waveforms and other sensor data that would not normally be used in order to conserve battery power.

As a second example, input 379 can be an ECG signal of the patient, which is the input used to determine whether or not the shock criterion is met. For example, a rhythm analysis of the ECG signal may be performed to determine whether or not the shock criterion is met. The rhythm analysis can be performed in a first manner if it is determined that breathing characteristic 335 meets an alert criterion, while the rhythm analysis can be performed in a second manner different than the first manner otherwise. The alert criterion may be that breathing characteristic 335 has a value that is within a safe range, exceeds a threshold, etc. Moreover, the first manner can be different from the second manner in a number of ways. For example, the first manner may include a first set of analyses of the ECG signal, while the second manner may include the first set of analyses plus at least one more analysis that is not included in the first set of analyses.

Examples of different breathing characteristics are now described.

Figure 5:
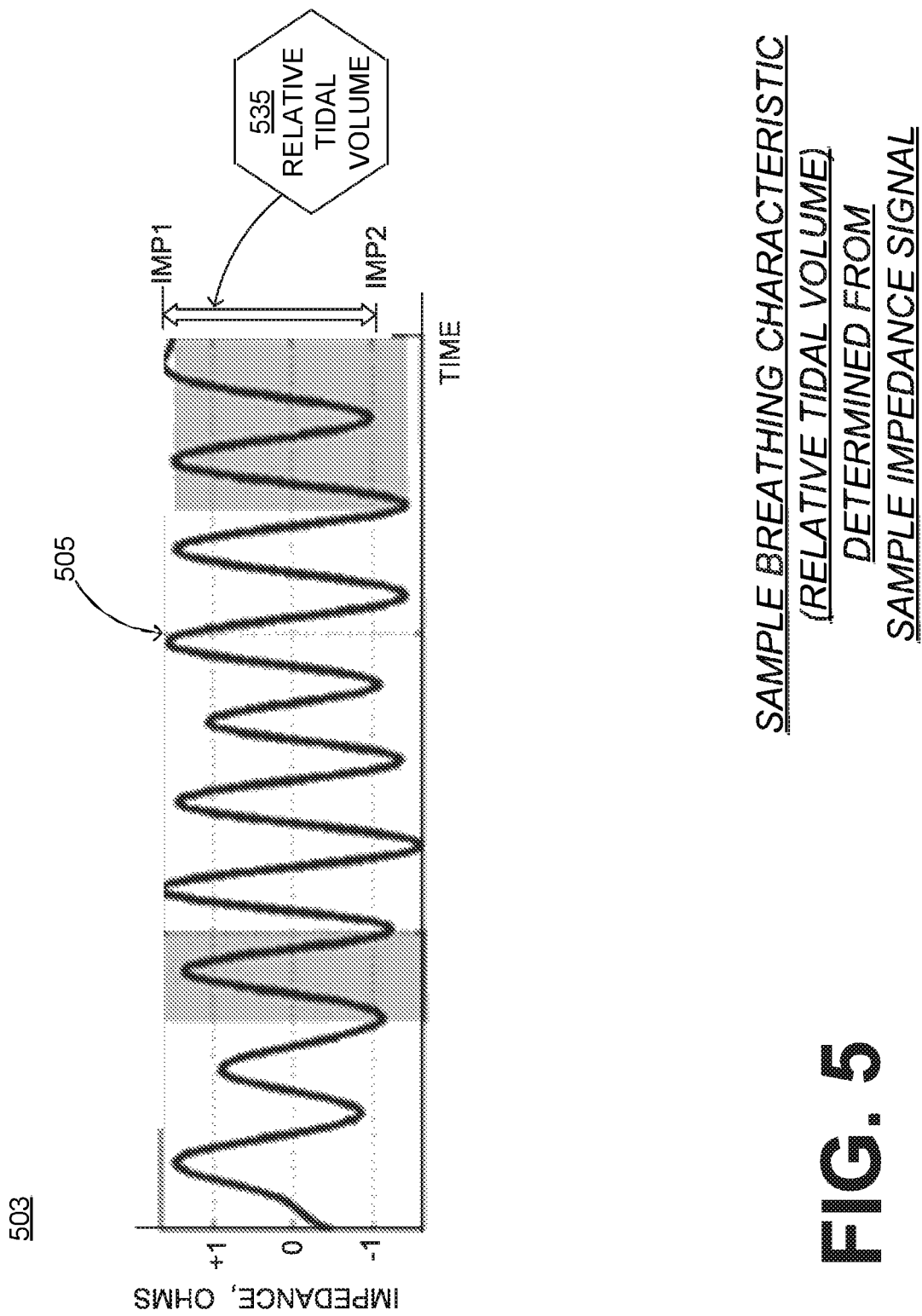
FIG. 5 is a time diagram of a sample impedance signal, annotated to illustrate how a breathing characteristic is determined according to embodiments.

For one example, the breathing characteristic can be a relative tidal volume. For instance, FIG. 5 is a time diagram 503 of a sample impedance signal 505. Impedance signal 505 may be as rendered from impedance detector 222, with or without the aforementioned filtering.

In diagram 503, signal 505 is annotated to illustrate how a breathing characteristic 535 may be determined. In particular, a relative amplitude of impedance signal 505 can be detected, such as the difference between impedance values IMP1 and IMP2. Then the relative tidal volume can be determined from the detected relative amplitude.

Further variations are possible, for computing a more accurate value of relative tidal volume 535. For example, a plurality of relative amplitudes of the impedance signal may be detected for a predetermined period of time, or for predetermined number of cycles. Then an average relative tidal volume may be determined from the plurality of detected relative amplitudes, and so on.

Figure 6:
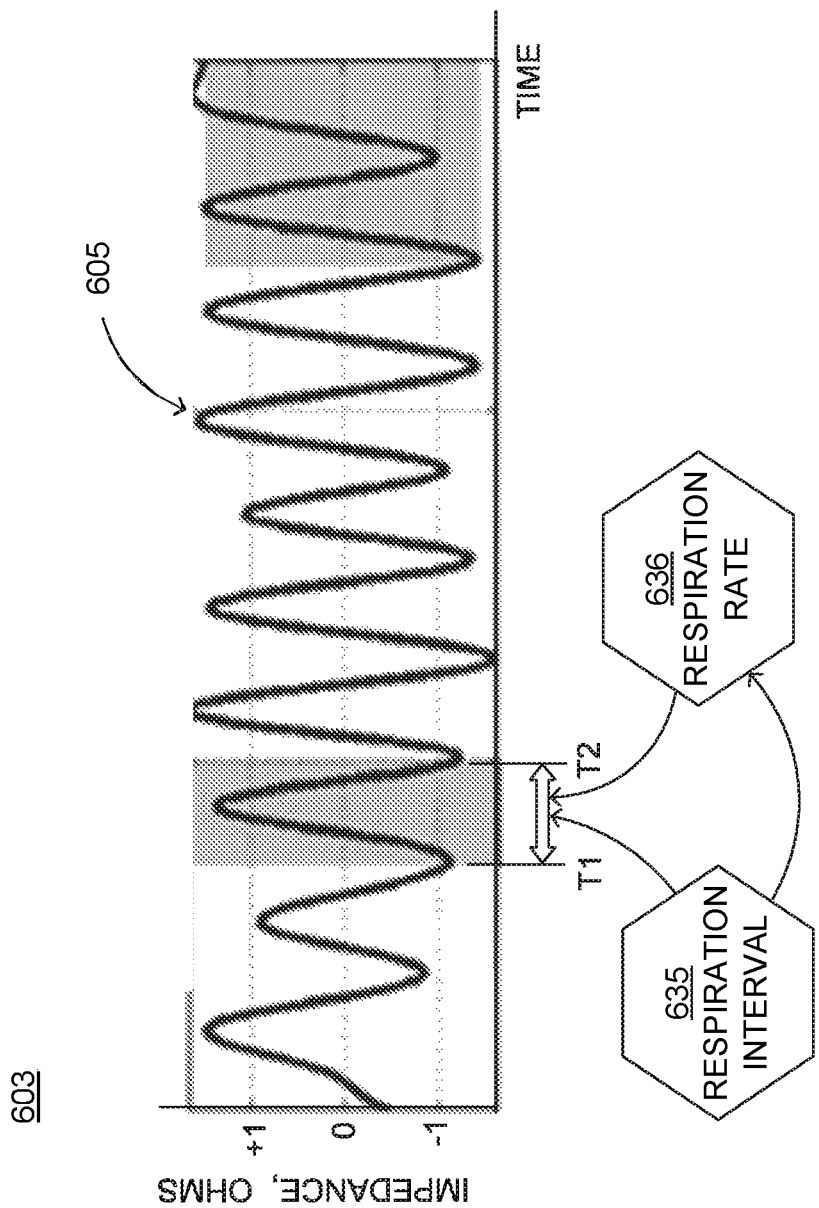
FIG. 6 is a time diagram of a sample impedance signal, annotated to illustrate how another breathing characteristic is determined according to embodiments.

For another example, the breathing characteristic can be a respiration interval or a respiration rate (RR). For instance, FIG. 6 is a time diagram 603 of a sample impedance signal 605. Impedance signal 605 may be as rendered from impedance detector 222, with or without the aforementioned filtering.

In diagram 603, signal 605 is annotated to illustrate how a breathing characteristic 635 may be determined. In particular, a period of impedance signal 605 can be detected, such as the difference between time values T1 and T2. Then the detected period can be treated as the respiration interval 635. Or, a respiration rate 636 may be determined from the detected period, or from respiration interval 635.

Further variations are possible, for computing a more accurate value for respiration rate 636. For example, a plurality of periods may be detected, an average may be taken, and so on as above. In some versions, it may not be possible to detect the respiration rate. Processor 230 may be further configured to determine whether or not the respiration rate is detectable, and determine that the shock criterion of operation 380 is met responsive to the respiration rate not being detectable.

The respiration rate (RR) may be used in combination with other sensors such as an accelerometer in the WCD system. For example, in combination with activity monitoring from an accelerometer, minimum RR variability may be considered a surrogate of ventilation at rest and maximum RR variability may be considered a measure of exercise ventilation. Orthopnea or orthopnoea is shortness of breath (dyspnea) that occurs when lying flat, causing the person to have to sleep propped up in bed or sitting in a chair. Orthopnea or paroxysmal nocturnal dyspnea (PND) may also be assessed from respiration rate assessment in combination with night time elevation angle as determined by an accelerometer.

Figure 7:
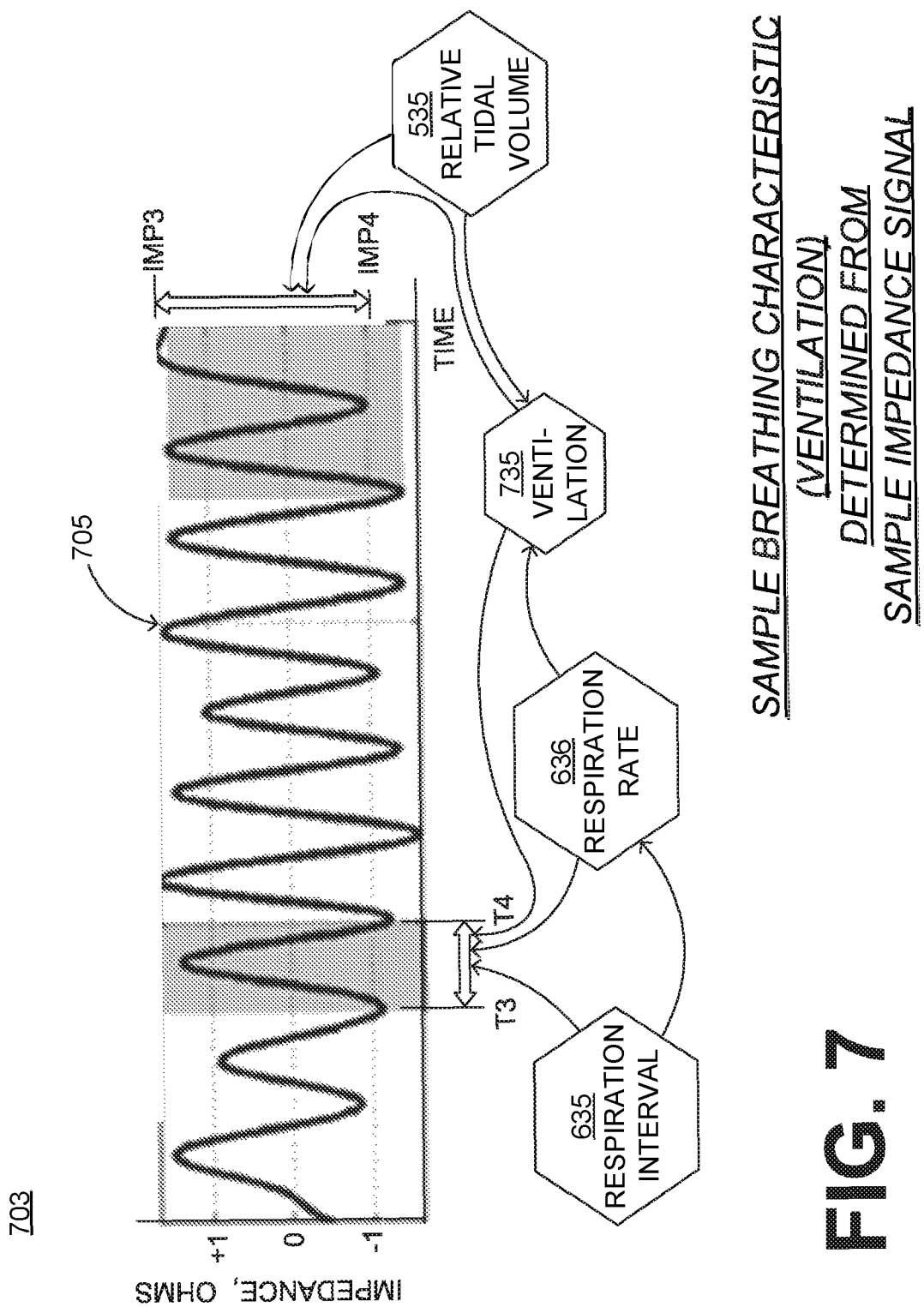
FIG. 7 is a time diagram of a sample impedance signal, annotated to illustrate how one more breathing characteristic is determined according to embodiments.

For one more example, the breathing characteristic can be a ventilation that the patient is receiving. For instance, FIG. 7 is a time diagram 703 of a sample impedance signal 705. Impedance signal 705 may be as rendered from impedance detector 222, with or without the aforementioned filtering.

In diagram 703, signal 705 is annotated to illustrate how a ventilation 735 may be determined. In particular, a relative amplitude of impedance signal 705 can be detected, such as the difference between impedance values IMP3 and IMP4. Moreover, a period of impedance signal 705 can be detected, such as the difference between time values T3 and T4. Then ventilation 735 can be determined from the detected relative amplitude and from the detected period.

It will be further recognized, also thanks to further annotations in FIG. 7, that ventilation 735 can alternately become known from relative tidal volume 535, respiration interval 635 and respiration rate 636. Moreover, all written above for improvements in computing these breathing characteristics may be applied similarly for computing ventilation 735.

Additional statistics may be computed for breathing characteristic 335, with or without the added information about motion events that can be contributed by motion detection signal 405. For example, the processor may be further configured to determine a range of acceptable respiration rates of the patient, a minimum respiration rate, a maximum respiration, a median respiration rate, and so on. Trends of these can also be detected and stored. For example, when these are tracked over a day, week or even longer, they may be used as an indicator of important physiologic changes such as dyspnea (a clinical manifestation of heart failure), or as a predictor for worsening heart failure decompensation.

Alveolar ventilation (a product of respiratory rate and tidal volume) is normally carefully controlled by the actions of central and peripheral chemoreceptors and lung receptors. Ventilation is driven by both the arterial partial pressure of oxygen ($PaO_2$) and the arterial partial pressure of carbon dioxide ($PaCO_2$), with $PaCO_2$ being the more important driver of the two. The body attempts to correct hypoxaemia and hypercarbia by increasing both tidal volume and respiratory rate. Thus, these conditions can be detected by measuring the respiratory rate.

Any condition that causes metabolic acidosis, such as abdominal pathology or sepsis, will also precipitate an increase in tidal volume and respiratory rate through an increased concentration of hydrogen ions, which leads to increased $CO_2$ production. In addition, other conditions that could cause hypercarbia or hypoxia may also increase alveolar ventilation. In effect, the respiratory rate can be an important indicator of a severe derangement in many body systems, not just the respiratory system, and can therefore be a key predictor of adverse events.

Of course, not all causes of hypoxia and hypercarbia necessarily result in an increase in tidal volume and respiratory rate. Medications such as opiates, which are commonly used in hospitals, depress the respiratory drive and the respiratory response to hypoxia and hypercarbia. In these circumstances the respiratory rate can still be a useful tool to monitor for an adverse event, as the respiratory rate may be lowered, often in association with a reduced level of consciousness.

Returning briefly to FIG. 3, as already mentioned above, at operation 340 it is optionally determined whether or not breathing characteristic 335 meets an alarm condition. Furthermore, at operation 380 it is determined whether or not a shock criterion is met. For either one or both operations 340, 380, in a number of embodiments or versions it can be determined whether or not breathing characteristic 335 meets an alarm condition, and the determination of operations 340, 380 can be performed based at least in part responsive to breathing characteristic 335 meeting the alarm condition.

In a number of embodiments or versions, breathing characteristic 335 has a value, and it can be determined that the breathing characteristic meets the alarm condition if that value meets a numerical condition. Examples are now described.

FIG. 8 shows how operations 840, 880 may be performed in terms of a diagram 803. Otherwise, operations 840, 880 may be performed as operations 340, 380 of FIG. 3 respectively.

Diagram 803 shows a single vertical axis with two sample thresholds, TH1 and TH2. The breathing characteristic has a value 835 that can be plotted at an appropriate location on the vertical axis, relative to thresholds TH1 and TH2. In other words, the determination of operations 840, 880 may be performed by answering the question-mark of dot 835. Accordingly, possible numerical conditions that can be used as a criterion for operations 840, 880 may include that a) value 835 is above threshold TH1, b) value 835 is within a range defined by thresholds TH1 and TH2, c) value 835 has a value that is below a threshold TH2, d) etc. For example, for respiration rate measurement, such thresholds TH1, TH2 etc. may be set in isolation or in combination with other sensors as also described elsewhere in this document.

Returning briefly to FIG. 3, if at operation 340 the answer is YES then, according to operation 345, a follow-up action may be caused to be executed. Examples include that executing the follow-up action includes a) that a record of the alarm condition being met is stored in a memory such as memory 238, b) a user interface such as user interface 280 outputs a communication to prompt the patient to react as instructed, c) a communication module such as communication module 290 transmits an alarm message wirelessly to alert medical personnel or other caregivers, and so on. Indeed, an abnormal respiratory rate has been shown to be an important predictor of serious events such as cardiac arrest.

In some embodiments, operations 340, 380 are performed responsive to a change in the value of breathing characteristic 335, or in a rate of change in the value of breathing characteristic 335. Examples are now described.

FIG. 9 shows how operations 940, 980 may be performed in terms of a diagram 903. Otherwise, operations 940, 980 may be performed as operations 340, 380 of FIG. 3 respectively.

Diagram 903 shows a graph 935 that indicates a sample evolution of a value of the breathing characteristic. At times T11, T12, T13, the breathing characteristic has values V11, V12, V13 respectively.

In some embodiments, the processor can be configured to determine whether or not a change in a value of the breathing characteristic meets a change condition, i.e. whether V12-V11 or V13-V12 meets the change condition, for example by being larger than a threshold difference. If the change condition is met, the processor may cause a follow-up action to be executed (operation 940)—the follow-up action can be as above. And/or, if the change condition is met, the determination of whether or not the shock criterion is met (operation 980) can be performed based at least in part responsive to the change condition being thus met.

In some embodiments, the processor can be configured to determine whether or not a rate of change in a value of the breathing characteristic meets a rate-of-change condition. In other words, assuming that T12-T11=T13-T12, it can be determined whether or not the contrast of V13-V12 and V12-V11 meets a rate-of-change condition. An example of meeting such a condition is if V13-V12 is larger than V12-V11 by a threshold. If the rate-of-change condition is met, the processor may cause a follow-up action to be executed (operation 940)—the follow-up action can be as above. And/or, if the rate-of-change condition is met, the determination of whether or not the shock criterion is met (operation 980) can be performed based at least in part responsive to the rate-of-change condition being thus met.

In the methods described above, each operation can be performed as an affirmative step of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

In this description a single reference numeral may be used consistently to denote a single item, aspect, component, or process. Moreover, a further effort may have been made in the drafting of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

What is claimed is:

1. A method for a wearable cardioverter defibrillator (WCD) system, the WCD system including a processor, a power source, a support structure worn by a patient, an energy storage module configured to store an electrical charge, a discharge circuit, and an impedance detector configured to render an impedance signal of the patient, and a memory, the method comprising:
   receiving the impedance signal indicative of an impedance of the patient from the impedance detector;
   filtering the impedance signal to derive a filtered impedance signal, wherein filtering the impedance signal comprises removing one or more impedance signal variations that repeat for at least 30 seconds; determining, from the filtered impedance signal, a characteristic of breathing by the patient;
   receiving an electrocardiogram (ECG) signal of the patient; determining, from at least the breathing characteristic and analysis of the ECG signal, whether or not a shock criterion is met, further comprising:
   storing a baseline value for the breathing characteristic;
   computing a difference of a current value of the breathing characteristic and the stored baseline value; and
   determining at least in part that the shock criterion is met responsive to the computed difference of the current value and stored baseline value being larger than a threshold;
   analyzing the ECG signal in a first manner when the breathing characteristic meets an alert criterion;
   determining at least in part that the shock criterion is met responsive to the ECG analysis in the first manner;
   analyzing the ECG signal in a second manner different from the first manner when the breathing characteristic does not meet the alert criterion; and determining at least in part that the shock criterion is met responsive to the ECG analysis in the second manner; and
   responsive to the shock criterion being met, delivering a shock to the patient.

2. The method of claim 1, in which
the WCD system further includes a memory; and
further comprising:
storing the current and baseline values of the breathing characteristic in the memory.

3. The method of claim 1, further comprising:
   receiving a motion detection signal indicative of a motion of the patient;
   wherein the baseline value is determined from a portion of the impedance signal and the motion detection signal.

4. The method of claim 1, further comprising:
receiving a motion detection signal indicative of a motion of the patient; and
determining from at least the motion detection signal and the breathing characteristic whether or not the shock criterion is met.

5. The method of claim 1, in which the breathing characteristic comprises a relative tidal volume; and
further comprising:
detecting a relative amplitude of the impedance signal; and
determining the relative tidal volume from the detected relative amplitude.

6. The method of claim 1, in which
the breathing characteristic comprises a respiration interval, and
further comprising:
detecting a period of the impedance signal; and
treating the detected period as the respiration interval.

7. The method of claim 1, in which
the breathing characteristic comprises a respiration rate, and
further comprising:
detecting a period of the impedance signal; and
determining the respiration rate from the detected period.

8. The method of claim 7, further comprising:
determining whether or not the respiration rate is detectable; and
determining that the shock criterion is met at least in part responsive to the respiration rate not being detectable.

9. The method of claim 1, in which
the breathing characteristic comprises a ventilation, and further comprising:
detecting a relative amplitude of the impedance signal;
detecting a period of the impedance signal; and
determining the ventilation from the detected relative amplitude and from the detected period.

10. The method of claim 1, further comprising:
determining whether or not the breathing characteristic meets an alarm condition; and
causing a follow-up action to be executed responsive to determining that the alarm condition is thus met.

11. The method of claim 10, in which the breathing characteristic meets the alarm condition if the breathing characteristic has a value that meets a numerical condition.

12. The method of claim 10, in which
the WCD system further includes a memory; and
executing the follow-up action includes storing a record of the alarm condition being met in the memory.

13. The method of claim 10, in which
the WCD system further includes a user interface; and
executing the follow-up action includes that the user interface outputs a communication.

14. The method of claim 10, in which the WCD system further includes a communication module; and
executing the follow-up action includes that the communication module transmits an alarm message.

15. The method of claim 1, further comprising:
determining whether or not the breathing characteristic meets an alarm condition; and
in which the determination of whether or not the shock criterion is met is performed based at least in part responsive to the breathing characteristic meeting the alarm condition.

16. The method of claim 15, in which the breathing characteristic meets the alarm condition if the breathing characteristic has a value that meets a numerical condition.

17. The method of claim 1, further comprising:
determining whether or not a change in a value of the breathing characteristic meets a change condition; and
causing a follow-up action to be executed responsive to determining that the change condition is thus met.

18. The method of claim 1, further comprising:
determining whether or not a rate of change in a value of the breathing characteristic meets a rate-of-change condition; and
causing a follow-up action to be executed responsive to determining that the rate-of-change condition is thus met.

19. The method of claim 1, further comprising:
determining whether or not a change in a value of the breathing characteristic meets a change condition; and
in which the determination of whether or not the shock criterion is met is performed based at least in part responsive to the change condition being thus met.

20. The method of claim 1, further comprising:
determining whether or not a rate of change in a value of the breathing characteristic meets a rate-of-change condition; and
in which the determination of whether or not the shock criterion is met is performed based at least in part responsive to the rate-of-change condition being thus met.

21. The method of claim 1, wherein the one or more impedance signal variations are selected from a movement of an electrode, a movement of the patient, a shift of a baseline of the impedance signal, noise, or a combination thereof.

22. An external defibrillator system, comprising:
an external defibrillator configured to be attached to a patient by the patient, the external defibrillator comprising:
an energy storage module configured to receive an electrical charge from a power source, and to store the received electrical charge;
a discharge circuit coupled to the energy storage module;
an accelerometer;
an impedance sensor;
a wireless communication module;
a transducer configured to render an electrocardiogram (ECG) signal of the patient;
a memory; and
a processor operatively coupled to the memory and configured to:
receive an accelerometer output signal from the accelerometer,
receive an impedance signal from the impedance sensor,
filter an impedance signal to derive a filtered impedance signal, wherein filtering the impedance signal comprises removing one or more impedance signal variations that repeat for at least 30 seconds; determine, using the accelerometer output signal and the filtered impedance signal, a characteristic of breathing by the patient,
store a baseline value for the breathing characteristic in the memory,
determine a deviation of the breathing characteristic from the baseline value for the breathing characteristic,
perform a shock analysis based on the ECG signal and the breathing characteristic to determine whether a shock criterion is met, the determination of whether the shock criterion is met being influenced by the determination that the deviation of the breathing characteristic substantially deviates from the baseline value for the breathing characteristic exceeds a predetermined threshold, and control, responsive to the shock criterion being met, the discharge circuit to discharge the stored electrical charge through the patient while a support structure is attached to the patient; and another device configured to receive information derived from the ECG signal with the external defibrillator via the wireless communication module.

23. The external defibrillator system recited in claim 22, wherein the external defibrillator is a Wearable Cardioverter Defibrillator.

24. The external defibrillator system recited in claim 22, wherein the baseline value for the breathing characteristic is a set value.

25. The external defibrillator system recited in claim 22, wherein the baseline value for the breathing characteristic is a value customized to the patient.

26. The external defibrillator system of claim 22, wherein the one or more impedance signal variations are selected from a movement of an electrode, a movement of the patient, a shift of a baseline of the impedance signal, noise, or a combination thereof.

\* \* \* \* \*